(12) United States Patent
Wiese et al.

(10) Patent No.: US 6,492,564 B1
(45) Date of Patent: *Dec. 10, 2002

(54) PROCESS FOR THE CATALYTICALLY CARRYING OUT MULTIPHASE REACTIONS, IN PARTICULAR HYDROFORMYLATIONS

(75) Inventors: Klaus-Diether Wiese, Haltern (DE); Guido Protzmann, Marl (DE); Juergen Koch, Haltern (DE); Dirk Roettger, Recklinghausen (DE); Martin Trocha, Essen (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/585,425

(22) Filed: Jun. 2, 2000

(30) Foreign Application Priority Data

Jun. 2, 1999 (DE) .......................................... 199 25 384

(51) Int. Cl.$^7$ .............................................. C07C 45/00
(52) U.S. Cl. ...................... 568/451; 568/452; 568/453; 568/454
(58) Field of Search ................................. 568/453, 452, 568/451, 454

(56) References Cited

U.S. PATENT DOCUMENTS 4,577,043 A * 3/1986 Kalbfell et al.

FOREIGN PATENT DOCUMENTS

| DE | 27 15 685 | 10/1977 |
|----|-----------|---------|
| DE | 32 34 701 | 5/1984 |

OTHER PUBLICATIONS

US patent Application 09/583,776.*
McMurry , J. Organic Chemistry, 2nd edition, 1988.*
S. Ergun, Chemical Engineering Progress, Carnegie Institute of Technology, vol. 48, No. 2, pps. 89–94, "Fluid Flow Through Packed Columns," Feb. 1952.
Y. Sato, et al., Journal of Chemical Engineering of Japan, vol. 6, No. 2, pps. 147–152, "Pressure Loss and Liquid Holdup in Packed Bed Reactor with Cocurrent Gas–Liquid Flow," 1973.
D.E. Sweeney, AlChE Journal, vol. 13, No. 4, pps. 663–669, "A Correlation of Pressure Drop in Two–Phase Cocurrent Flow in Packed Beds," Jul. 1967.
V.W. Weekman, Jr., et al., A.l.Ch.E. Journal, vol. 10, No. 6, pps. 951–957, "Fluid–Flow Characteristics of Concurrent Gas–Liquid Flow in Packed Beds," Nov. 1964.
R.P. Larkins, et al., A.l.Ch.E. Journal, vol. 7, No. 2, pps. 231–239, "Two–Phase Concurrent Flow in Packed Beds," Jun. 1961.
N. Midoux, et al., Journal of Chemical Engineering of Japan, vol. 9, No. 5, pps. 350–356, "Flow Pattern, Pressure Loss and Liquid Holdup Data in Gas–Liquid Downflow Packed Beds with Foaming and Nonfoaming Hydrocarbons," 1976.
VDI Wärmeatlas, 7$^{th}$ Expanded Edition, La1–La2, Lb1–Lb7, Lc1–Lc9, Ld1–Ld11, Le1–Le4, Lf1–Lf9, Lga1–Lga3, Lgb1–Lgb7, "VDI–Verlag GmbH," 1994.
H. Brauer, Grundlagen der Einphasen– und Mehrphasenströmungen, pps. 713–762, "Gas–Flüssigkeits–Strömungen in Rohren," 1971.
H. Brauer, Grundlagen der Einphasen– und Mehrphasenströmungen, pps. 763–791, Gas–Flüssigkeits–Strömungen in Füllkörperschchten, 1971.
H. Brauer, Grundlagen der Einphasen– und Mehrphasenströmungen, pps. 792–798, "Gas–Flüssigkeits–Strömungen in Füllkörperschichten," 1971.

* cited by examiner

*Primary Examiner*—Alan L. Rotman
*Assistant Examiner*—Hector M Reyes
(74) *Attorney, Agent, or Firm*—Oblon, Spivak, McClelland, Maier & Neustadt, P.C.

(57) ABSTRACT

The invention relates to a catalytic process for carrying out multiphase reactions in a tubular reactor, with the catalyst being present in the continuous phase and at least one starting material in a disperse phase and the loading factor B of the tubular reactor being equal to or greater than 0.8. The process is especially suitable in particular for the hydroformylation of olefins. The aldehydes thus prepared can ideally be used for the preparation of alcohols, carboxylic acids or in aldol condensations.

19 Claims, 1 Drawing Sheet

PROCESS FOR THE CATALYTICALLY CARRYING OUT MULTIPHASE REACTIONS, IN PARTICULAR HYDROFORMYLATIONS

BACKGROUND OF THE INVENTION

1. Field of the Invention

The present invention relates to a process for carrying out multiphase reactions in a tubular reactor, in particular for preparing aldehydes by reacting olefinically unsaturated compounds with hydrogen and carbon monoxide in the presence of a catalyst.

2. Discussion of the Background

Aldehydes are used in the synthesis of many organic compounds. Their direct secondary products are alcohol and carboxylic acids which are used industrially. The alcohols prepared from the aldehydes are used, inter alia, as solvents and as a precursor for the preparation of plasticizers and detergents.

It is known to prepare aldehydes and alcohols by reacting olefins with carbon monoxide and hydrogen. The reaction is catalyzed by hydrido metal carbonyls, preferably those of metals of group 8 of the Periodic Table of the Elements. In addition to cobalt, which is used industrially to a broad extent as catalyst metal, rhodium has recently achieved increasing importance. In contrast to cobalt, rhodium permits the reaction to be carried out at relatively low pressure. The hydrogenation of the olefins to give saturated hydrocarbons is markedly less when rhodium catalysts are used than when cobalt catalysts are used.

In the case of the processes carried out industrially, the rhodium catalyst is formed during the process from a catalyst precursor, synthesis gas and, if appropriate, other ligands having a modifying action. In the case of use of modified catalysts, the modifying ligands can be present in the reaction mixture in excess. Ligands which have proved particularly expedient are tertiary phosphines or phosphates. Their use enables the reaction pressure to be decreased to values below 300 bar.

However, in the case of the above process, problems arise in separating off the reaction products and recovering the catalysts which are homogeneously dissolved in the reaction product. Generally, for this purpose, the reaction product is distilled off from the reaction, mixture. In practice, this route, because of the thermal sensitivity of the catalyst or the products formed, can only be taken in the event of the hydroformylation of lower olefins having up to about 5 carbon atoms in the molecule.

On an industrial scale, $C_4$ and $C_5$ aldehydes are prepared, for example in accordance with DE 3234701 or DE 2715685.

In the latter process, the catalyst is dissolved in the organic phase which is composed of product and high-boilers (resulting from the product). Olefin and synthesis gas are introduced into this mixture. The product is discharged from the reaction together with the synthesis gas, and in a more recent variant taken off as liquid. Since the catalyst slowly decays in its output, a portion must continuously be discharged together with high-boilers and replaced by an equivalent amount. Because of the high cost of rhodium, recovering the rhodium from the discharge stream is essential. The workup process is complex and thus burdens the process.

According to DE 3234701, this disadvantage is overcome, for example, by the catalyst being dissolved in water. The water solubility of the rhodium catalyst used is achieved by using trisulfonated triarylphosphines as ligands. Olefin and synthesis gas are passed into the aqueous phase. The product resulting from the reaction forms a second liquid phase. The liquid phases are separated outside the reactor and the catalyst phase separated off is recycled to the reactor.

Technically, the above two processes are multiphase reactions.

Multiphase reactions are taken below to mean reactions that proceed with the participation of two or more immiscible, or only partially miscible, fluid phases. This includes, for example, reactions between a gas phase and a liquid phase (gl), between two liquid phases which are immiscible or have a miscibility gap (ll) and reactions in which both two liquid immiscible, or only partially miscible, phases and one gas phase participate (gll).

However, in addition, the use of other fluid phases, e.g. supercritical phases, is also conceivable. A supercritical phase of this type can occur alternatively to said phases, but also additionally.

Examples of industrially important gas-liquid reactions (gl) are, in addition to the hydroformylation of liquid olefins in the presence of a catalyst dissolved in organic phase, the reaction of acetylene with carboxylic acids or hydrogenations with homogeneously dissolved catalysts or oxidations with air or oxygen.

The above-noted examples share the problem of mass transfer, since the reaction partners are present in different phases. In the case of hydroformylation in the 3-phase system, the process procedure is particularly difficult, since the starting materials are present in three separate phases.

Not only olefin but also synthesis gas must be transported into the aqueous catalyst phase in order to come into contact there with the catalyst. Finally, backtransport out of the aqueous phase must take place. Since the transport processes are frequently slower than the actual reaction, such reactions are determined by the rate of mass transfer, and one speaks of a transport-inhibited reaction.

Multiphase reactions are associated with a series of problems which makes them considerably more difficult to carry out industrially than is the case with simple homogeneous reactions. Some typical problems are mentioned below:

In all cases, the substances must be brought into contact with one another as intimately as possible in order to minimize the problem of mass transfer: a mass transfer area $a_s$ as large as possible must be generated between the phases. On the other hand, the phases must be able to be easily separated again after reaction is completed. Too intensive a mixing can lead to problems here. When two liquid phases are present, emulsion formation can occur, and in the case of gas-liquid processes foaming can occur. In the 3-phase process mentioned, all problems can even occur simultaneously.

In addition to a high mass transfer surface area, $a_s$, as high as possible a mass transfer coefficient $k_1$ should be achieved in all multiphase reactions. Overall, what is termed the KLA value, i.e. the product of $k_1$ and $a_s$, in the mass transfer equation $$j = k_l * a_s * (C^* - C)$$

where j (mol/s) is the molar flow rate of the reacting component passing through the phase interface, $k_l$ (m/s) is the mass transfer coefficient, $a_s$ (m²) is the phase interface area in the reactor, C* (mol/m³) is the maximum solubility of the starting material in the second phase, and C (mol/m³) is the actual concentration of the starting material, which in turn is coupled to the reaction rate, should be a maximum.

Another problem in the case of multiphase reactions is heat dissipation with exothermic reactions. If the reaction rate is successfully increased by improving the mass transfer, obviously, more heat must be dissipated, which can lead to an unwanted temperature increase up to reaction runaway.

These problems of the multiphase reaction can be solved technically, e.g. by using a stirred-tank reactor.

For the hydroformylation of olefins, the use of a stirrer under elevated pressure is disadvantageous, since in this case a fault-susceptible shaft seal must be provided. In addition, in this process, a plurality of stirrers must be used in order to achieve adequate phase mixing.

The high heat of reaction produced in hydroformylations can generally only be controlled by using heat exchangers mounted in the interior of the reactor.

The use of a stirred tank always leads to back-mixing, which decreases the effective concentration of the reactants, which leads to lowering the space-time yield. This disadvantage must be paid for by the capital expenditure on expensive reaction space.

During the hydroformylation of olefins, the space-time yield decreases sharply anyway with increasing number of carbon atoms in the olefin. The correlation between molecular size and reaction rate is known (B. Cornils, W. Herrmann, Aqueous-Phase Organometallic Catalysis, Concepts and Application, Verlag Wiley-VCH, pp. 308–310). Thus, for example, the ratio of hydroformylation reaction rates of 1-pentene to 1-hexene is 2.6/1. A conversion of higher olefins therefore becomes increasingly uneconomic.

In view of the above considerations, there is a need for a process that avoids the abovementioned disadvantages and which, in addition, can be implemented industrially in a simple manner.

SUMMARY OF THE INVENTION

It is an object of the present invention to provide a process for carrying out multiphase reactions which is especially suitable for preparing aldehydes by means of catalytic hydroformylation of olefins.

This object and other objects have been achieved by the present invention, which provides a process that includes carrying out a multiphase reaction catalytically in a tubular reactor, the multiphase reaction including a continuous phase and at least one disperse phase, wherein a catalyst is present in the continuous phase and at least one starting material is present in the disperse phase, and wherein the tubular reactor includes a loading factor, B, that is equal to or greater than 0.8.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein FIG. 1 diagrammatically shows a preferred embodiment of an apparatus for the hydroformylation of olefins.

Figure 1:
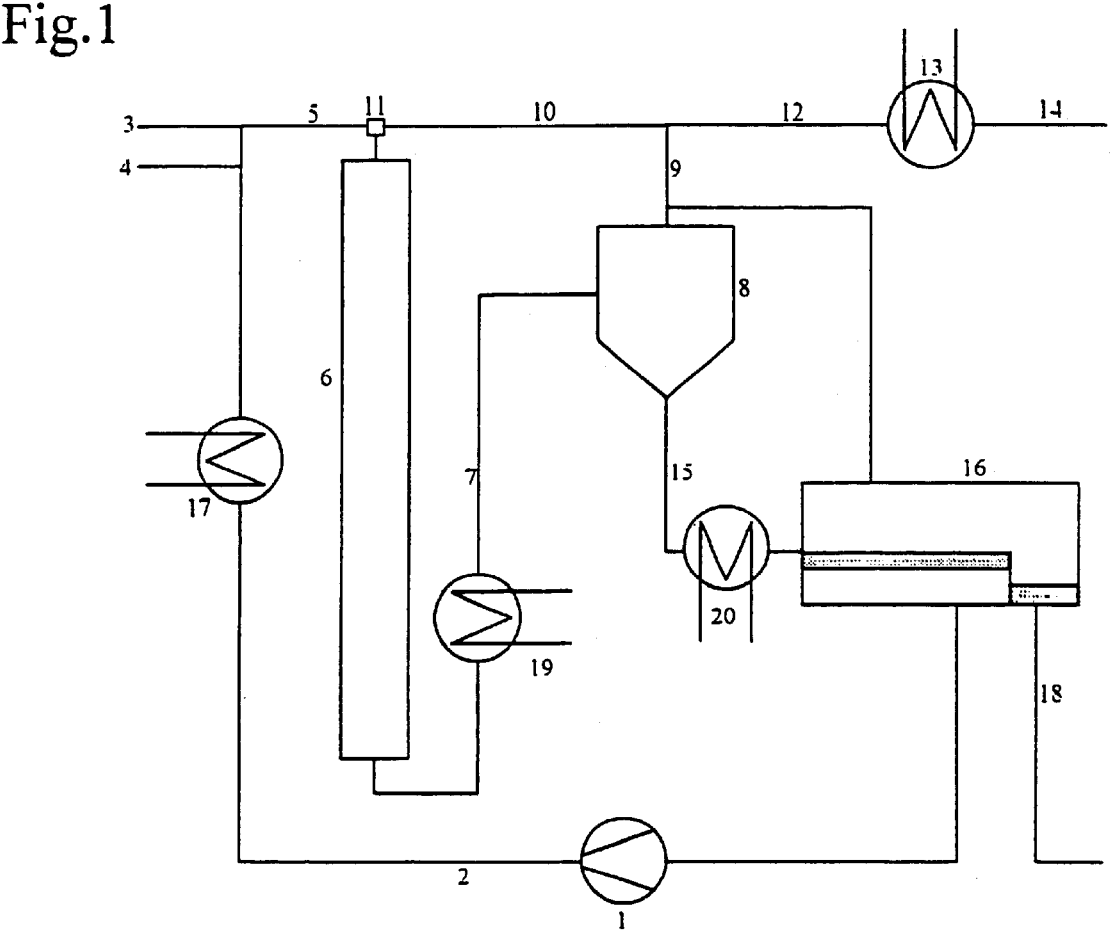
In FIG. 1, the aqueous catalyst is circulated by pumping by a pump 1. Olefin 3 and synthesis gas 4 are added to the catalyst phase 2. The multiphase mixture 5 is pumped through the tubular reactor 6 which is provided with static elements. The resulting mixture 7, including product, unreacted starting material and the catalyst, is degassed in the gas separator 8. The gas 9, which includes synthesis gas, if appropriate gaseous olefin and enriched inert substances is for the most part fed again to reactor 6 via a gas recycle line 10 using a mixture nozzle or jet nozzle 11. A small portion of the gas steam 9 is ejected via line 12. By suitable cooling 13 and return, olefin losses can be minimized. The ejection 14 is reduced to enriched inert substances and small amounts of unreacted synthesis gas.

The liquid stream 15 arising after the degassing 8 is passed into a phase separation vessel 16. Here the aqueous catalyst phase 2 is separated off and fed back to the circulation. The heat of reaction can be dissipated via heat exchangers 17, 19, 20 lying outside the reactor. the product is taken off via line 18 and if appropriate further purified.

DETAILED DESCRIPTION OF THE INVENTION

Various other objects, features and attendant advantages of the present invention will be more fully appreciated as the same becomes better understood from the following detailed description of the preferred embodiments of the invention.

Technically, the novel process should preferably comply with the following requirements of a multiphase process:

generation of high and stable mass transfer between the participating phases simple to carry out, as far as possible with conventional industrial apparatuses simple and safe heat dissipation high operation reliability simple and secure scaling up.

With respect to the preparation of aldehydes to be carried out, in addition the following are especially preferred:

high selectivity, avoidance in particular of high-boiling byproducts no, or only slight, catalyst discharge high space-time yield, small reactors high product purity.

By means of the process according to the invention, a surprisingly simple process has been found for carrying out multiphase reactions which can be carried out in a tubular reactor—if appropriate filled with random packing elements or internals—and is suitable for the hydroformylation of olefins using synthesis gas with high space-time yields and selectivities.

The invention therefore relates to a process for carrying out multiphase reactions catalytically in a tubular reactor, with the catalyst being in the continuous phase and at least one starting material being present in a disperse phase and the load factor B of the reactor being equal to or greater than 0.8.

In a preferred embodiment of the present invention, olefins are hydroformylated, i.e. reacted with synthesis gas to form aldehydes, via the multiphase reaction.

The tubular reactor used in the process of the invention can include random packing elements or internals. Random packing elements in the context of the present invention include, for example: Raschig rings, saddles, Pall rings, tellerettes, wire mesh rings, wire mesh cloth. Examples of internals are filter plates, flow breakers, column trays, perforated plates or other mixing apparatuses. However, internals in the context of the present invention which are also conceivable are a plurality of narrow tubes connected in parallel, a multitube reactor thus resulting. Particular preference is given to structured mixer packings or demister packings.

It is especially preferable in the process of the invention to maintain or exceed a minimum cross sectional loading of the tubular reactor. In the case of upwards mode operation of the reactor (flow direction from bottom to top), the flooding point should preferably be exceeded. The reactor is thus operated above the point at which bubble columns are customarily operated. In the case of downwards mode operations (flow direction from top to bottom), the cross sectional loading is preferably set in such a manner that the reactor is completely flooded. Operation is therefore preferably carried out above the point at which one can still speak of a trickle bed phase.

To establish more precisely the minimum loading of the reactor which is to be maintained, the load factor B of the tubular reactor is calculated as a dimensionless pressure drop of:

$$B=PD/PS,$$

where PD (Pa/m) is a pressure dropper unit length over the reactor under operating conditions and PS (Pa/m) is an operand having the dimension of a pressure per unit length, defined as ratio or mass flow rate M (kg/s) of all components in the reactor to the volumetric flow rate V (m³/s) of all components under operating conditions multiplied by g (9.81 m/s²), i.e. PS=(M/V)*g.

Clearly PS should preferably be the static pressure per meter of a multiphase mixture in a vertically upright tube if all phases were to flow with the same velocity. PS is a pure operand which results from the flow rates fed to the reactor and which can be specified independently of the flow direction of the reactor, the flow velocity of all phases or the flooding state of the reactor.

The pressure drop PD (Pa/m) is used as an operand in order to specify the process conditions and can be calculated according to the customary methods for single or multiphase flows. Customary processes for calculating the pressure drop PD in tubes, internals or dumped packing beds etc. can be looked up for example, in VDI-Wärmeatlas (VDI Atlas of Heat) 7th expanded edition, VDI-Verlag GmbH, Düsseldorf 1994, sections Lal to Lgb7, and in the standard work Heinz Brauer, Grundlagen der Einphasen- und Mehrphasenströmungen (Fundamentals of Single-phase and Multiphase Flows), Verlag Sauerländer, Aarau and Frankfurt am Main, 1971. The entire contents of each of the above-noted references is hereby incorporated by reference.

The pressure drop in the case of single-phase flow through an empty tube is given by $$PD=Cw*\rho/2*w^2/D$$

where
- $\rho$ (kg/m³) is the density of the flowing medium under operating conditions,
- w (m/s) is the flow velocity (volumetric flow rate/cross sectional area),
- D (m) is the tube diameter, and
- Cw (–) is the drag coefficient of the tube through which flow passes.

In the case of flow through random packing elements, arranged packings or internals, the velocity w must be replaced by the effective velocity (w/ψ) and the tube diameter D by the hydraulic channel diameter $d_H$ of the random packing elements or internals, so that the following applies:

$$PD=Cw\rho/2*(w/\psi)^2 1/d_H$$

where
- $d_H$ (m) is the hydraulic channel diameter,
- ψ (–) is the void content, and
- Cw (–) is the drag coefficient of the packed apparatus with flow.

The packing-specific data $d_H$ and ψ are frequently a component of the delivery specifications of packings. Data are specified for a number of packings in the abovementioned VDI-Wärmeatlas.

The void content ψ can also be determined experimentally by, for example, gauging the capacity in liters of the reactor before and after charging with the packings. The hydraulic channel diameter in turn can, if it is unknown, be calculated from the specific surface area F (m²/m³) of the random packing elements or internals (generally known or experimentally determinable by one of ordinary skill in this art) according to the simple relationship $$d_H=4\psi/F.$$

The drag coefficient of tubes, internals and random packing elements is generally described as a function of the Reynolds number Re, which gives information on the flow state under the chosen conditions. In the case of random packing elements, internals etc., the relationship below is virtually always applicable:

$$Cw=K_1/Re^n+K_2/Re^m$$

where frequently n=1, m=0 (approach according to S. Ergun, Chem. Engng. Progr. 48, (1948), 89, the entire contents of which being hereby incorporated by reference), or n=1, m=0.1 (approach according to Brauer et al.). $K_1$, $K_2$ are packing-specific constants which are known from the delivery data or from the literature (examples can be found in the VDI-Wärmeatlas and in Brauer et al.). However, they can also be determined experimentally by operating the tubular reactor containing random packing elements with a liquid under different velocities and determining Cw as a function of Re from the known data and the measured pressure drop.

The dimensionless Reynolds number Re finally is defined as Re=w*(ρ/η)*D for empty tubes and Re=(w/ψ)*(ρ/η)*$d_H$ for tubes containing internals or random packing elements. η(Pa*s) denotes in each case the viscosity and ρ (kg/m³) denotes the density of the flowing medium.

The pressure drop in the case of two-phase flows (here gas-liquid for synthesis gas/catalyst solution) increases super proportionately. Generally, according to Lockhart-Martinelli (in Brauer et al.), the entire contents of which being hereby incorporated by reference, the pressure drop of the two-phase flow $P_{lg}$ is based on the pressure drop of one of the two phases, for example on the pressure drop of the pure flowing liquid phase $P_l$, and related to the ratio of the pressure drop of the two phases $P_l$ and $P_g$ thought of as flowing alone.

To calculate pressure drops in two-phase flows, frequently dimensionless pressures are used according $\phi^2=P_{lg}/P_l$ and $X^2=P_l/P_g$. The further correlation $\phi^2$=function ($X^2$) is frequently studied. Examples can be found in the following literature references, the entire contents of each of which being hereby incorporated by reference:

Y. Sato, T. Hirose, F. Takahashi, M. Toda: "Pressure Loss and Liquid Hold Up in Packed Bed Reactor with Cocurrent Gas-Liquid Down Flow"; J. Chem. Eng. of Japan, Vol. 6 (No. 2), 1973, 147–152; D. Sweeney: "A Correlation for Pressure Drop in Two-Phase Concurrent Flow in Packed Beds"; AIChE-Journal, Vol. 13, 7/1967, 663–669; V. W. Weekman, J. E. Myers: "Fluid-Flow Characteristics of Concurrent Gas-Liquid Flow in Packed Beds"; AIChE-Journal, Vol. 10 (No. 6), 11/1964, 951–957; R. P. Larkins, R. P. White, D. W. Jeffrey: "Two-Phase Concurrent Flow in Packed Beds"; AIChE-Journal, Vol. 7 (No. 2) 6/1961, 231–239 or N. Midoux, M. Favier, J.-C. Charpentier: "Flow Pattern, Pressure Loss and Liquid Holdup Data in Gas-Liquid Down-Flow Packed Beds with Foaming and Nonfoaming Liquids"; J. Chem. Eng. of Japan, Vol. 9 (No. 5), 1976, 350–356.

Preferably, the relationship proposed by Midoux, which has been checked for many gas-liquid systems, is used for the calculation. In the case of nonfoaming systems, this is, for example $$\phi^2 1 + 1/X + 1.14/X^{0.54}$$

This relationship named after Lockhart-Martinelli is shown graphically in many works, detailed treatments thereof can be found in many textbooks of process engineering and publications, as well as in Brauer et al.

The pressure drop of the two-phase flow $P_{gl}$ results from the experimentally determined pressure drop or pressure drop estimated as described above of the pure flowing liquid phase $P_l$ then by $$P_{gl} = \phi^{2*} P_l$$

In the special case of the preparation of aldehydes by hydroformylation of olefins, the calculation of the pressure drop becomes still more complex. In addition to the synthesis gas phase and a liquid catalyst phase, the presence of organic liquid phase must be taken into account. This problem can be taken into account by determining a further dimensionless pressure $\phi^2_{org} = P_{gll}/P_{lg}$, so that the pressure drop must be determined as below:

$$P_{gll} = \phi^{2*} \phi^2_{org} * P_l.$$

Generally, with a reactor length L (m) the following applies $$PD = P_{gl}/L \text{ or } PD = P_{gll}/L$$

The pressure drop of a multiphase flow can thus be calculated via conventional means of chemical process engineering. The same applies to the above-defined dimensionless pressure drop B, i.e. the loading factor of the multiphase reactor.

The size of the dimensionless loading factor B is a necessary basic condition of the process of the invention; B should be greater than or equal to 0.8, preferably greater than or equal to 0.9, or particularly preferably greater than or equal to 1.

In the range B is greater than or equal to 0.8, a reactor operated from top to bottom begins to flood. Reference may be expressly made to the fact that when these conditions are complied with, the advantages of the process of the invention are also achieved if the reactor is operated from bottom to top or in another direction.

Higher cross sectional loadings of the reactor (B>>1), recognizable by an increasing pressure differential over the reactor, are possible at any time and even desirable provided that the increasing space-time yields justify the energy consumption which increases to the same extent. An upper limit is therefore only given by practical considerations such as energy consumption or difficulties in the separation of the phases when the reaction is complete.

It can thus be seen that in addition to the volumetric flow rates of the individual phases or the superficial velocities derived therefrom $w = V/(\pi D^2/4)$ the dimensions of the reactor (length L, diameter D) and, in particular, the data of the packings used (hydraulic diameter $d_H$, void content L) play an important role. Via the correct choice of these parameters, the process can be adapted without difficulty to the most varied requirements; it is only of importance to comply with the requirement B>=0.8, Preferably B>=0.9 and particularly preferably B>=1.

In the case of a slow reaction, for example, the hydraulic diameter of the random packing elements is preferably chosen to be small or their specific surface area is chosen to be high, so that the required conditions for B are already achieved at low flow velocities. In this manner sufficient residence times are achieved over the length of a reactor which is dimensioned expediently industrially. In the case of very rapid reactions, a reverse procedure is preferred.

A further preferred criterion when carrying out the process of the invention is the ratio of the mass flow rate of the liquid catalyst-containing phase $M_1$ to the mass flow rate of the disperse phase or phases $M_2$. In the case of hydroformylation, the mass flow rate of the catalyst phase $M_1$ is preferably substantially greater than the mass flow rate of the disperse phases, i.e. the organic olefin phase $M_{2a}$ and the synthesis gas phase $M_{2b}$. In the process of the invention the mass ratio $M_1/M_2$ of the continuous phase ($M_1$) to the disperse phases ($M_2$) can be greater than 2, for example $M_1/M_2 > 10$ applies. Flow conditions where $M_1/M_2 > 100$ are absolutely possible and are frequently even advantageous. Under the condition $M_1/M_2 > 2$, the catalyst phase is the continuous phase, while the disperse phases are divided into fine bubbles or into fine droplets. In the process of the invention it possible that at least one starting material is dispersed by the energy introduced into the tubular reactor by the continuous phase. This leads to a distribution of at least one starting material in bubbles or droplets within the continuous catalyst phase.

This can also be estimated via conventional engineering means. Suitable approaches for this are those having dimension parameters such as $$d_s/d_h = k * Re_{gl(gll)}^m * We_{gl(gll)}^n$$

where
- $d_s$ is the diameter of the droplets or bubbles according to Sauter (in Brauer et al.)
- $d_H$ is the hydraulic random packing element diameter,
- $Re_{gl(gll)}$ the Reynolds number of the multiphase flow= $w_{gl(gll)} * (\rho_l/\eta_l) * (d_H/L)$,
- $We_{gl(gll)}$ is the Weber number of the multiphase flow= $w_{gl(gll)}^2 * (\rho_l/\sigma_{gl}) * (d_H/L^2)$,
- k, m, n are empirical constants (known or to be determined by experiments within the ordinary skill of the artisan),
- w is the superficial velocities $(m/s) = V/(\pi D^2/4)$,
- V is the volumetric flow rate under operating conditions $(m^3/s)$,
- $\rho$ is the density under operating conditions $(kg/m^3)$,
- $\eta$ is the viscosity under operating conditions $(Pa*s)$ and
- $\gamma$ is the interfacial tension under operating conditions $(N/m)$ and the indices are l (liquid phase), g (gas phase), gl (gas/liquid two-phase flow) and gll (gas/liquid/liquid three-phase flow).

In the case of structured packings such as Sulzer SMV or narrow tubes as internals, it is plausible that a calculated or droplet diameter d, greater than the channel diameter is not rational. However, this does not apply to permeable packings and random packing elements, for example wire mesh rings or wire mesh cloth (so-called demister packings or mist eliminators). In the process of the invention, calculated droplet diameters can be used which are at least equal to less than the hydraulic channel diameter:

$d_s/d_H <= 1$, preferably <0.9.

From the calculated droplet diameter, finally, a mass transfer surface area may be calculated from $A_s = 6 \psi_g d_s (m^2/m^3)$.

For the phase content $\psi$ of the disperse phase (in the case of hydroformylation synthesis gas and organic phase are dispersed), the following can be set $\psi_g \sim W_g/W_{gl}$ using the superficial velocities of the phases.

The residence time $\tau$ of the phases flowing through the reactor may be calculated approximately from $\tau \sim L\psi/W_{lg}$. The residence time $\tau$ in the process of the invention is generally far less than one hour and can be in the range of minutes or even below. Nevertheless, in the case of this completely unusual mode of operation—high catalysts throughput in the reactor, comparatively very low content of starting material in the reaction mass, causing in turn very short residence time—in many multiphase reactions, surprisingly high space-time yields are achieved. Alternatively, markedly lower temperatures than usual can be employed for the same space-time yields, since the increase in reaction rate which, for example, can be accompanied by minimization of secondary reactions and thus improved selectivity, permits this economically.

The process of the invention can be flexibly adapted to the most varied requirements. For special requirements, the following embodiments of the process of the invention are preferred:

If the application requires a very long mixing zone or if static zones are required, for example for taking off substance streams, a cascade arrangement of tubular reactors having internals or random packing elements is preferable.

A cascade of tubular reactors or the alternative disposition of packed and empty tube sections is preferable if an especially low pressure drop is desirable.

In addition, the parallel disposition of tubular reactors or the use of a multitube reactor, in which case the tubes can adopt the function of the internals, is preferable.

Furthermore, reactors having a multiple feed of gas over the reactor length can be provided if the gas consumption is so high that unfavorable phase ratios of gas to liquid result when the two phases are combined upstream of the reactor.

The special conditions of the process of the invention permit further embodiments of the process. Thus the high necessary circulation of the catalyst phase or of the continuous phase can be exploited in addition to the operation of a jet nozzle which is disposed as liquid jet gas compressor upstream of the actual tubular reactor. This can be used for thorough premixing of the two phases and for compressing the gas phase which makes possible the mode of operation at relatively high inlet pressures in the reactor. Finally, if, vice versa, instead of the compression of the gas the suction action is exploited, a recirculation of gas with simultaneous premixing of the phases is even possible. The energy introduced into the tubular reactor via the catalyst-containing continuous phase can thus be used for dispersing the starting material phase or at least one starting material.

The heat dissipation in the case of highly exothermic reactions, for example in the case of hydroformylation, is also not limited in the process of the invention. The high throughput of the catalyst circulation acts as a heat carrier, so that even in the case of the adiabatic mode of operation of the reactor, only small temperature differences occur and a homogeneous temperature distribution in the reactor results without temperature peaks. The heat generated may then be conveniently dissipated by a conventional heat exchanger disposed anywhere in the external catalyst circuit, or exploited for energy production. For improved heat dissipation, under some circumstances, it may be expedient to run the catalyst circulation rate still higher (that is at higher B value) than is necessary according to the experimental results, since a lower temperature gradient over the reactor can be set via the catalyst circulation rate.

The process of the invention, in comparison with known methods, offers considerable advantages, which may be mentioned as follows:

At comparatively low temperatures, high space-time yields can be achieved.

Formation of byproducts is extremely low, and values of 1–2% by weight and below are possible.

The catalyst is treated mildly, the deactivation is very low and a continuous discharge is avoided.

In the case of preparation of aldehydes by hydroformylation of olefins, further advantages result with the use of the process of the invention:

Owing to the increased reaction rate, this process can also be used economically for hydroformylating higher olefins having more than 10 carbon atoms.

In the case of gaseous olefins, the starting material portion remaining after a partial reaction can be recirculated by simple recycling by means of a jet nozzle.

An especially preferred embodiment of the present invention, a process for hydroformylating olefins by synthesis gas in a multiphase system, may be described in more detail. The continuous phase used is the catalyst phase and it is pumped through a tubular reactor by means of a pump.

Particularly preferred solvents for preparing the catalyst solution and phase include all those solvents which comply with the following conditions:

The solvent is sparingly soluble in the product phase.

The product dissolves only sparingly in the catalyst phase which includes catalyst and solvent.

The solvent has a sufficiently high solubility for the catalyst used.

The solvent can include as additive phase-transfer reagents, surface-active reagents or amphiphilic reagents or surfactants. The preferred solvent used is water.

The hydroformylation catalysts used can be metals of subgroup 8 of the Periodic Table of the Elements (Fe, Co, Ni, Ru, Rh, Pd, Os, Ir, Pt). These metals or compounds of these metals should be soluble in the catalyst phase, but not the product phase, under the reaction conditions. If aqueous catalyst solutions are used, this necessitates water-soluble metal compounds. The preferred catalyst used is rhodium or water-soluble rhodium compounds. Suitable rhodium salts are for example rhodium (III) sulfate, rhodium (III) nitrate, rhodium (III) carboxylates such as rhodium acetate, rhodium propionate, rhodium butyrate or rhodium 2-ethylhexanoate.

The type of ligands preferably depends on the metal used and solvent of the catalyst solution. These complexes must be catalytically active and not lose their catalytic activity in long-term operation. A preferred condition of this is that the ligands do not alter, for example by reaction with the solvent.

Preferred ligands used for the catalytically active metals can be triarylphosphines. Especially preferable phosphines have one or two phosphorus atoms which have three aryl radicals per phosphorus atom, the aryl radicals being identical or different and representing a phenyl, naphthyl, biphenyl, phenylnaphthyl or binaphthyl radical, in particular phenyl, biphenyl or binaphthyl radical. The aryl radicals can be bonded directly to the phosphorus atoms or via a —(CH$_2$)$_x$ group, where x is an integer from 1 to 4, preferably from 1 to 2, particularly preferably 1. For water-soluble catalyst systems, ligand should preferably contain three —(SO$_3$)M radicals, where M is identical or different and is H, an alkali metal ion, an ammonium ion, a quaternary ammonium ion, (by calculation half) an alkaline earth metal ion or zinc ion.

The —SO$_3$M radicals are preferable substituents on the aryl radicals and give the triarylphosphines the required water solubility. A preferred sulfonated triarylphosphine containing one phosphorus atom is trisodium tri-(m-sulfophenyl)phosphine.

In addition to the sulfonato units (—SO$_3$M), other polar groups, for example carboxylato units, can also be used.

The aqueous phase can be used directly in the hydroformylation or it can be subjected in advance to a preformation of the catalyst under reaction conditions in order then to use it in preformed form. The aqueous catalyst solution may be prepared in a relatively simple manner, however, by dissolving a water-soluble metal salt and the water-soluble ligands in water and complexing them.

Preferably, the metal salt concentration in the process of the invention can be set over a broad range. The highest value is predetermined by the solubility. The reaction rate also preferably depends on the metal salt concentration. Generally, at higher metal salt concentrations, higher reaction rates are achieved. On the other hand, higher metal salt concentrations mean higher costs. Therefore, depending on reactivity of the starting material and the other reaction conditions, an optimum can be chosen. The rhodium content in the catalyst phase is preferably 20 ppm to 2000 ppm, more preferably 100 to 1000 ppm.

In the catalyst system used, the molar ratio between metal and ligands can be varied in order to achieve the optimum for each individual reaction. This ratio is preferably between ⅕ and 1/200, more preferably between 1/10 and 1/60.

The pH of the catalyst solution can be optimized for the hydroformylation of each olefin with respect to selectivity of aldehyde formation. It is preferably between 2 and 8, more preferably between 3.0 and 5.5.

Starting material which can be used for the hydroxyformylation are olefnic compounds preferably having 2–25 carbon atoms, more preferably 2–12 carbon atoms. The olefinic compounds can contain one or more carbon-carbon double bonds, each of which may be disposed terminally or internally. Preference is given to olefinic compounds having a terminal carbon-carbon double bond. An olefin of uniform structure can be used in the process. Olefin mixtures can also be used. The mixture can include isomeric olefins of the same number of carbon atoms or olefins of a differing number of carbon atoms or of a mixture which includes both isomeric olefins and olefins of a differing number of carbon atoms. In addition, the olefins or olefin mixtures can include under reaction conditions inert substances such as aliphatic hydrocarbons.

In the process of the invention olefins from the most varied sources can be used. For example, olefins from cracking processes, dehydrogenations or from the Fischer-Tropsch synthesis may be mentioned. Likewise, suitable starting materials are olefins or olefin mixtures which have been formed by dimerization, oligomerization, codimerization, cooligomerization or metathesis of olefins. The olefins used can (under standard conditions) be gaseous, liquid or solid. Solid olefins are used as solutions. The solvents used are inert liquids which are scarcely soluble in the catalyst phase. Particular preference is given to solvents which have a higher boiling point than the product to be prepared, since by this means separation off by distillation and recirculation are facilitated.

Preferably, α-olefnic compounds are used in the process of the invention. Examples of preferable α-olefinic compounds include 1-alkenes, alkyl alkenoates, alkylene alkanoates, alkenyl alkyl ethers and alkenols, for example propene, butene, pentene, butadiene, pentadiene, 1-hexene, 1-heptene, 1-octene, 1-nonene, 1-decene, 1-undecene, 1-dodecene, 1-hexadecene, 2-ethyl-1-hexene, 1,4-hexadiene, 1,7-octadiene, 3-cyclohexyl-1-butene, styrene, 4-vinylcyclohexene, allyl acetate, vinyl formate, vinyl acetate, vinyl propionate, allyl methyl ether, vinyl methyl ether, vinyl ethyl ether, allyl alcohol, 3-phenyl-1-propene, hex-1-en-4-ol, oct-1-en-4-ol, 3-butenyl acetate, allyl propionate, allyl butyrate, n-propyl 7-octenoate, 7-octenoic acid, 5-hexenamide, 1-methoxy-2,7-octadiene, 3-methoxy-1,7-octadiene, and especially preferably propene, 1-butene, technically available mixtures which essentially includes 1-butene, 2-butene and isobutene, and/or 1-pentene.

Products of the hydroformylation of olefins are aldehydes and appropriate alcohols which are longer by one carbon atom. The aldehydes prepared by the process of the invention can be used for preparing alcohols by hydrogenation. The resultant alcohols are in turn precursors for plasticizers, for example as phthalic diesters or detergents.

In addition, the aldehydes prepared by the process of the invention are especially suitable in aldol condensations and in the preparation of carboxylic acids by oxidation.

Preferable hydroformylation agents include mixtures of hydrogen and carbon (synthesis gas) or other mixtures of hydrogen, carbon monoxide substances inert under reaction conditions.

When liquid olefins or solid olefins in solution are used it is preferable to use the hydroformylation agent in excess so that as complete a degree of conversion as possible is achieved. This decreases the workup expenditure. When gaseous olefins are used it can, in contrast, be expedient to use a deficiency of hydroformylation reagent, since excess gaseous olefin separates from the liquid product and can be recirculated back to the process.

The molar ratio of olefin to hydrogen and olefin to carbon monoxide can be greater than, less than or equal to 1.

The process of the invention, in the case of hydroformylation when a gaseous olefin is used, is firstly a two-phase reaction, with a product phase forming during the reaction and thus a three-phase system being formed. When a liquid olefin is used, a three-phase system is present from the beginning.

The process of the invention can be carried out in one or more tubular reactors having internals corresponding to the preceding description.

In the process of the invention, the catalyst phase is the continues phase; a mass ratio between catalyst phase and the disperse phase or phases in the preferable range from 2/1 to 3500/1, more preferably in the range 40/1 to 2500/1, is therefore expedient.

If the process of the invention is used for the hydroformylation olefins, the mass ratio between catalyst phase and olefinic phase at the reactor inlet is preferably in the range of 5000/1 to 4/1, more preferably in the range of 2000/1 to 50/1. The mass ratio between catalyst phase and hydroformylation agent (generally synthesis gas) is preferably 4/1 to 10,000/1, more preferably 200/1 to 4000/1.

The reactants can be fed preheated, i.e. in the range of the reaction temperature, or can be fed cold. Owing to the high phase ratio with the catalyst phase, the preheating may also be performed via the process heat.

If the process of the invention is used for the hydroformylation of olefins, the reaction is preferably performed in a temperature range of 20° C. to 250° C., more preferably in the range of 90° C. to 150° C.; in this case the overall pressure is preferably between 10 bar and 300 bar, more preferably between 20 bar and 150 bar.

Flow can pass through the reaction tube concurrently from top to bottom or vice versa. For safety reasons, preference is given to charging from the top.

The heat of reaction can be dissipated via various heat exchangers. The heat exchangers in this case need not be in the vicinity of the reaction space, but can also be optionally outside the reactor. The individual heat fluxes are dependent on the specific heat of reaction and on the desired temperature in the reactor and in the apparatuses.

The heat of reaction dissipated can thus be simply utilized, for example in the process itself, for heating a distillation device or for generating steam.

The mixture leaving the reactor can be degassed in the event of use of gaseous olefins or in the event of an incomplete conversion in a gas liquid separation vessel. The gas-liquid separation can be performed at the same pressure as prevails at the reactor outlet. This is particularly advantageous when at least a portion of the expansion gas is recirculated to the reactor. Otherwise, expansion can also be performed at lower pressure (down to 1 bar).

The gas stream separated off can be wholly or partly recirculated to the reactor. This recirculation can be achieved in a known manner, for example by a jet or mixing nozzle which is mounted upstream of the reactor in the catalyst circulating stream, or by a circulating gas compressor. From energetic considerations, preferably a jet or mixing nozzle which mounted upstream of the reactor in the catalyst circulating stream is used. Preferably, the continuous phase is introduced into the reactor via a jet nozzle either upstream of the reactor or directly into the reactor. Preferably, the starting material is dispersed by the energy introduced into the reactor by the continuous phase.

The remaining amount of gas, or optionally all of the gas can be introduced cooled or uncooled into an exhaust gas utilization system. When a cooler is used, the gas condensate arising in the cooler can be passed via a line to the gas-liquid separation vessel. The degassed liquid mixture is mechanically separated in a liquid-liquid separation vessel into the catalyst phase and the product phase can be performed in settling vessels of various types of centrifuges. For reasons of cost, preference is given to settling vessels.

The residence times in the separation apparatus are preferably kept short. This has the following advantages: the separation apparatus is small and capital costs thereof are correspondingly low. With short residence times virtually no side reactions occur in the separation vessel. So that the phase separation proceeds rapidly, the density differences between the two phases must be sufficiently high and their viscosity must be low. All four parameters are a function of temperature and can readily be determined by preliminary experiments.

Furthermore, the density and viscosity of the catalyst solution can be varied by selecting the solvent and catalyst concentration. As a further possibility, the density and viscosity of the product phase can be altered by adding a solvent.

The phase separation can be performed in a broad temperature range. In this case the separation temperature can also be higher than temperature of the reaction discharge at the reactor outlet. For energetic reasons, however, it is not expedient to use a temperature higher than the liquid temperature in the gas separator. The preferred temperature to be considered is the setting point of one of the two liquid phases. With respect to short separation times, however, excessively low temperatures are less preferred, as mentioned above.

The product stream is preferably fractionated by known processes, e.g. by distillation.

Preferably, the catalyst solution separated off is, if appropriate after ejection of a small partial quantity and corresponding replacement by fresh catalyst solution, recycled to the reactor.

EXAMPLES

Having generally described this invention, a further understanding can be obtained by reference to certain specific examples which are provided herein for purposes of illustration only and are not intended to be limiting unless otherwise specified.

Hydroformylation of Olefins

The hydroformylation of olefins took place in an experimental apparatus which is shown diagrammatically in FIG. 1. Herein, the aqueous catalyst is circulated by pumping by a pump 1. Olefin 3 and synthesis gas 4 are added to the catalyst phase 2. The multiphase mixture 5 is pumped through the tubular reactor 6 which is provided with static elements. The resulting mixture 7, including product, unreacted starting material and the catalyst, is degassed in the gas separator 8. The gas 9, which includes synthesis gas, if appropriate gaseous olefin and enriched inert substances is for the most part fed again to reactor 6 via a gas recycle line 10 using a mixture nozzle or jet nozzle 11. A small portion of the gas steam 9 is ejected via line 12. By suitable cooling 13 and return, olefin losses can be minimized. The ejection 14 is reduced to enriched inert substances and small amounts of unreacted synthesis gas.

The liquid stream 15 arising after the degassing 8 is passed into a phase separation vessel 16. Here the aqueous catalyst phase 2 is separated off and fed back to the circulation. The heat of reaction can be dissipated via heat exchangers 17, 19, 20 lying outside the reactor, the product is taken off via line 18 and if appropriate further purified.

Examples 1–7 describe the hydroformylation of propene by the process of the invention.

Examples 1–5

A reactor 6 having a length of 3 m and a diameter of 17.3 mm was used which includes static mixer elements from Sulzer having a hydraulic diameter of 2 mm.

For this example the line 10 for recycling the gas was closed. The solvent used for the catalyst was water. The pH was 7. The flow through the reactor was at a temperature of 120° C. at a catalyst loading of 400 kg/h. The reaction pressure was 50 bar. The catalyst used was rhodium at a concentration of 800 ppm based on the solvent phase. The ligand used was tri(m-sulfophenyl)phosphine (TSTPP) in the form of its sodium salt, and the P/Rh ratio was 60. For Experiment 2, the reaction conditions of Experiment 1 were set except that the reaction temperature was 130° C. For Experiment 3 the reaction conditions of Experiment 1 were set except that the reaction pressure was 70 bar. For Experiment 4 the reaction conditions of Example 1 were set except that the pH of the catalyst solution was set to 4. For Experiment 5 the reaction conditions of Example 1 were set except that the catalyst loading of the reactor was 300 kg/h. The starting material streams fed to the reactor and the product streams are given in the table in mol/h.

| Example | 1 | 2 | 3 | 4 | 5 |
|---|---|---|---|---|---|
| Space-time yield (t/(m$^3$*h)) | 0.98 | 1.39 | 1.23 | 1.00 | 0.71 |
| B | 13.16 | 13.14 | 13.16 | 13.16 | 8.06 |

-continued

| Example | 1 | 2 | 3 | 4 | 5 |
|---|---|---|---|---|---|
| Starting material | | | | | |
| CO | 22.79 | 16.99 | 28.24 | 23.92 | 12.73 |
| $H_2$ | 21.28 | 15.87 | 26.38 | 22.87 | 11.89 |
| $N_2$ | 0.12 | 0.09 | 0.15 | 0.10 | 0.07 |
| Propene | 51.49 | 35.57 | 31.13 | 36.01 | 33.45 |
| Propane | 0.17 | 0.12 | 0.10 | 0.11 | 0.11 |
| Product | | | | | |
| CO | 2.15 | 2.09 | 2.08 | 0.66 | 2.11 |
| $H_2$ | 0.89 | 0.93 | 0.98 | 0.37 | 0.97 |
| Propene | 3.35 | 6.73 | 3.04 | 3.45 | 4.00 |
| Isobutanal | 0.24 | 0.51 | 0.53 | 0.39 | 0.20 |
| n-Butanal | 5.46 | 11.03 | 9.82 | 6.19 | 4.66 |
| Isobutanol | <0.01 | <0.01 | <0.01 | <0.01 | <0.01 |
| n-Butanol | 0.07 | 0.07 | 0.07 | 0.06 | 0.07 |
| 2-Ethylhexanal | 0.09 | 0.03 | 0.08 | <0.01 | 0.02 |
| 2-Ethylhexenal | 0.26 | 0.19 | 0.18 | <0.01 | 0.09 |
| Exhaust gas | | | | | |
| CO | 9.50 | 3.06 | 13.23 | 13.72 | 6.81 |
| $H_2$ | 8.45 | 1.46 | 9.97 | 10.82 | 3.59 |
| $N_2$ | 0.29 | 0.10 | 0.09 | 0.10 | 0.16 |
| Propene | 37.37 | 13.56 | 17.72 | 19.47 | 36.93 |
| Propane | 0.17 | 0.10 | 0.17 | 0.10 | 0.09 |
| Isobutanal | 0.24 | 0.16 | 0.15 | 0.18 | 0.14 |
| n-Butanal | 4.59 | 3.13 | 2.72 | 2.62 | 2.56 |

Examples 6 and 7

These examples illustrate the use of the gas recycle line 10. By this means the loss of valuable materials via the exhaust gas line can be minimized. Already with these examples, conversion rates >90% can readily be achieved. On account of the cooler 13, the ejection of propene in the exhaust gas can be virtually completely prevented, so that propene exits only with the liquid product. The product 18 which is taken off from the phase separation vessel and still contains propene is worked up according to the prior art by stripping it out with the synthesis gas or separating it off by distillation. By this means propene conversions of >99% are possible without penalties in the space-time yield.

In Examples 6 and 7 flow passed through the reactor at a catalyst loading of 400 kg/h at a temperature of 120° C. The reaction pressure was 50 bar. The rhodium concentration was 800 ppm based on the solvent phase. The ligand used was TSTPP in the form of its sodium salt, and the P/Rh ratio was 60. The starting material streams fed into the reactor and the product streams are given in the table in mol/h.

| | Example | |
|---|---|---|
| | 6 | 7 |
| Space-time yield (t/(m³*h)) | 1.06 | 1.04 |
| B | 12.12 | 12.12 |

-continued

| | Example | |
|---|---|---|
| | 6 | 7 |
| Propene Conversion | 93.70% | 92.33% |
| Synthesis gas conversion | 92.09% | 90.27% |
| Feed | | |
| Starting material | | |
| CO | 10.41 | 10.23 |
| $H_2$ | 9.56 | 9.63 |
| $N_2$ | 0.07 | 0.07 |
| Propene | 12.42 | 12.43 |
| Propane | 0.07 | 0.07 |
| Product | | |
| CO | 1.27 | 1.65 |
| $H_2$ | 0.24 | 0.39 |
| Propene | 0.58 | 0.73 |
| Isobutanal | 0.86 | 0.77 |
| n-Butanal | 8.04 | 8.24 |
| Isobutanol | <0.001 | <0.001 |
| n-Butanol | 0.13 | 0.11 |
| 2-Ethylhexanal | 0.15 | 0.12 |
| 2-Ethylhexenal | 0.29 | 0.18 |
| Exhaust gas | | |
| CO | 0.18 | 0.09 |
| $H_2$ | 0.09 | 0.05 |
| $N_2$ | 0.01 | 0.01 |
| Propene | 0.10 | 0.09 |
| Propane | 0.003 | 0.002 |

Hydroformylation of 1-hexene

Example 8

This example describes the use of the process according to the invention for the continuous hydroformylation of 1-hexene. The course of conversion over a longer reactor was determined by reusing resultant crude product again and again. Values are thus obtained as from a reactor several meters long in which gas is added again after each 1 m. The solvent used for the rhodium catalyst was water. The flow through the reactor having a volume of 235 ml (1 m length) was at a catalyst loading of 400 kg/h at a temperature of 130° C. The reaction pressure was 30 bar. The rhodium concentration was 800 ppm based on the solvent phase. The ligand used was TSTPP in the form of its salt, and the P/Rh ratio was 60. The synthesis gas loading was on average 132.8 1 (S.T.P.)/h. The feed stream of the liquid starting material was set to 1.3 1/h. After 8 passages (=8 m of react length), a conversion rate of just 90% is reached, but the RZA is still 0.44 t/(m³*h) calculated over the entire reactor length.

This value is far above technically known data. The overall selectivity after 8 passages is virtually 93%.

| Number of passages | 1 | 2 | 3 | 4 | 5 | 6 | 7 | 8 |
|---|---|---|---|---|---|---|---|---|
| Overall conversion rate (%) | 19.1 | 36.9 | 49.8 | 59.8 | 68.5 | 76.5 | 82.9 | 86.8 |
| High boilers | 0 | 0.37 | 0.28 | 2.1 | 2.65 | 4.29 | 4.59 | 4.62 |

-continued

| Number of passages | 1 | 2 | 3 | 4 | 5 | 6 | 7 | 8 |
|---|---|---|---|---|---|---|---|---|
| Overall selectivity (%) | 85.1 | 89.1 | 91.7 | 92.1 | 92.4 | 92.8 | 93.1 | 92.9 |
| Overall space-time yield (t(m$^3$*)) | 0.748 | 0.743 | 0.689 | 0.619 | 0.568 | 0.521 | 0.486 | 0.444 |
| B | 14.26 | 14.26 | 14.26 | 14.26 | 14.26 | 14.26 | 14.26 | 14.26 |

Example 9

Hydroformylation of 1-decene

A reactor having a length of 6 m and a diameter of 17.3 mm was used which included static mixer elements from Sulzer 55 having a hydraulic diameter of 2 mm.

For this example, the line 10 for recycling the gas was closed. The solvent used for (the catalyst was water. The pH was 4.5. The flow was passed through the reactor at a catalyst loading of 400 kg/h at a temperature of 125° C. The reaction pressure was 70 bar. The rhodium concentration was 800 ppm based on the solvent phase. The ligand used was TSTPP in the form of its sodium salt, and the P/Rh ratio was 5. The starting material streams fed to the reactor and the product streams are given in the table in mol/h.

|  | Example 9 |
|---|---|
| Space-time yield (t(m$^3$*h)) | 0.05 |
| B | 13.96 |
| Starting material | |
| CO | 11.38 |
| H$_2$ | 10.52 |
| N$_2$ | 0.05 |
| 1-Decene | 7.12 |
| Product | |
| 1-Decene | 6.67 |
| Undecanal | 0.34 |
| 2-Methyldecanal | 0.11 |
| Exhaust gas | |
| CO | 10.36 |
| H$_2$ | 0.89 |
| N$_2$ | 0.05 |

Obviously, numerous modifications and variations of the present invention are possible in light of the above teachings. It is therefore to be understood that within the scope of the appended claims, the invention may be practiced otherwise than as specifically described herein.

This application is based on German patent application 19925384.6, filed Jun. 2, 1999, the entire contents of which are hereby incorporated by reference.

What is claimed is:

1. A process, comprising:
   carrying out a multiphase reaction catalytically in a tubular reactor, said multiphase reaction comprising a continuous phase and at least one disperse phase, wherein a catalyst is present in said continuous phase and wherein at least one starting material is present in said disperse phase, and wherein said tubular reactor comprises a loading factor, B, that is equal to or greater than 0.8, wherein said multiphase reaction comprises hydroformylating at least one olefin.

2. The process as claimed in claim 1, wherein said olefin comprises 2 to 25 carbon atoms.

3. The process as claimed in claim 1, wherein said catalyst comprises a metal of subgroup 8 in the Periodic Table.

4. The process as claimed in claim 1, wherein said catalyst is rhodium.

5. The process as claimed in claim 1, wherein said catalyst is a water-soluble rhodium compound.

6. The process as claimed in claim 1, wherein said continuous phase comprises water or a mixture of water and an organic solvent.

7. The process as claimed in claim 1, wherein said loading factor B is greater than or equal to 0.9.

8. The process as claimed in claim 1, wherein said loading factor B is greater than or equal to 1.0.

9. The process as claimed in claim 1, wherein a mass ratio of said continuous phase to said disperse phase is greater than 2.

10. The process as claimed in claim 1, further comprising more than one disperse phase.

11. The process as claimed in claim 10, wherein a mass ratio of said continuous phase to the disperse phases is greater than 2.

12. The process as claimed in claim 1, further comprising driving a jet nozzle upstream of said tubular reactor with said continuous phase.

13. The process as claimed in claim 1, further comprising dispersing said starting material by introducing said continuous phase into said tubular reactor.

14. The process as claimed in claim 1, wherein said hydroformylating produces an aldehyde.

15. The process as claimed in claim 14, further comprising preparing an alcohol from said aldehyde.

16. The process as claimed in claim 14, further comprising carrying out an aldol condensation with said aldehyde.

17. The process as claimed in claim 14, further comprising preparing a carboxylic acid from said aldehyde.

18. The process as claimed in claim 15, wherein said alcohol is prepared from said aldehyde by hydrogenation.

19. The process as claimed in claim 17, wherein said carboxylic acid is prepared from said aldehyde by oxidation.

* * * * *